(12) United States Patent
Hollister

(10) Patent No.: US 7,179,241 B2
(45) Date of Patent: Feb. 20, 2007

(54) PROTECTIVE SLING

(76) Inventor: Laura Hollister, 2090 Weiser Rd., Niles, MI (US) 49120

( * ) Notice: Subject to any disclaimer, the term of this patent is extended or adjusted under 35 U.S.C. 154(b) by 0 days.

(21) Appl. No.: 11/140,796

(22) Filed: May 31, 2005

(65) Prior Publication Data

US 2006/0270957 A1    Nov. 30, 2006

(51) Int. Cl.
*A61F 5/00*    (2006.01)
*A61F 13/00*   (2006.01)
*A61F 13/06*   (2006.01)

(52) U.S. Cl. .............. 602/4; 602/20; 602/62; 602/63

(58) Field of Classification Search .......... 602/4, 602/60, 61, 62, 63, 20; 224/157, 158, 159, 224/160, 161; 128/869, 878; D24/190
See application file for complete search history.

(56) References Cited

U.S. PATENT DOCUMENTS

| | | | | |
|---|---|---|---|---|
| 1,183,225 A * | 5/1916 | Overmeyer | ................. | 128/878 |
| 2,539,677 A * | 1/1951 | Teare | .............................. | 602/4 |
| 3,841,543 A * | 10/1974 | Bolton | ........................ | 224/158 |
| 4,622,961 A * | 11/1986 | Christensen | ................... | 602/4 |
| 4,716,895 A * | 1/1988 | Marques et al. | ................ | 602/4 |
| 4,878,490 A * | 11/1989 | Scott | ........................... | 602/20 |
| 4,895,142 A * | 1/1990 | Liptak | ............................ | 602/4 |
| 5,464,383 A * | 11/1995 | Padden et al. | ................ | 602/20 |
| 5,558,626 A * | 9/1996 | Holtzman et al. | ............. | 602/4 |
| 5,792,083 A | 8/1998 | Joslin | | |
| 6,030,354 A * | 2/2000 | Lakusiewicz | ................... | 602/4 |
| 6,102,877 A | 8/2000 | Joslin | | |
| 6,213,362 B1 * | 4/2001 | Lorenzini et al. | ........... | 224/158 |
| 6,770,044 B1 | 8/2004 | Joslin | | |
| 6,918,885 B2 * | 7/2005 | Moore et al. | ................... | 602/4 |
| 6,923,778 B1 * | 8/2005 | Cheng | ............................ | 602/4 |
| 2002/0156406 A1 * | 10/2002 | Moore et al. | ................... | 602/4 |

OTHER PUBLICATIONS

Joslin Orthopedic Gear, "Arm Sling Design," 1995-2005, www.armsling.com/design.
Joslin Orthopedic Gear, "The Ultimate Arm Sling," 1995-2005, www.armsling.com/index.

* cited by examiner

*Primary Examiner*—Henry Bennett
*Assistant Examiner*—Kari Petrik
(74) *Attorney, Agent, or Firm*—Barnes & Thornburg LLP

(57) ABSTRACT

A protective sling adapted to support a cast or brace extending adjacent a forearm and wrist, and to selectively simultaneously support a hand of a patient. The sling being made of a flexible material having a first portion extending a predetermined length, and a second portion partially overlying the length of the first portion and forming an opening into a sleeve, the sleeve disposed between the first portion and the second portion. The sleeve having a closed end opposite to and spaced from the opening between the first and second portions forming the sleeve. A strap assembly is attached to the closed end and to an opposite end of the protective sling, the strap assembly adapted to extend adjacent the neck and shoulder of the patient, suspending the protective sling adjacent the body of the patient.

4 Claims, 4 Drawing Sheets

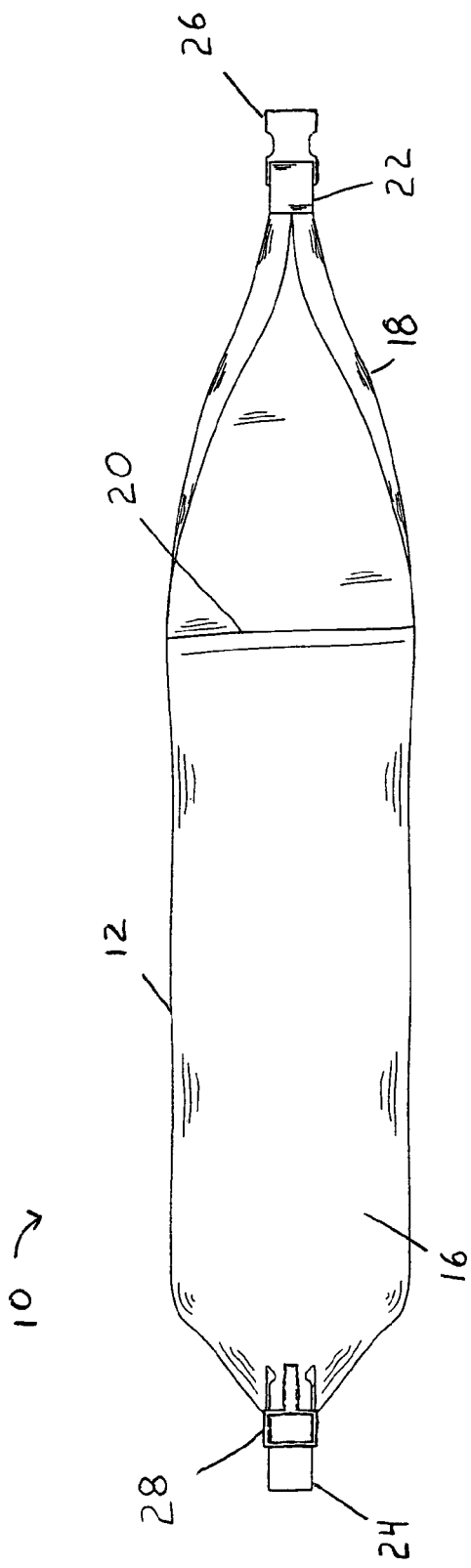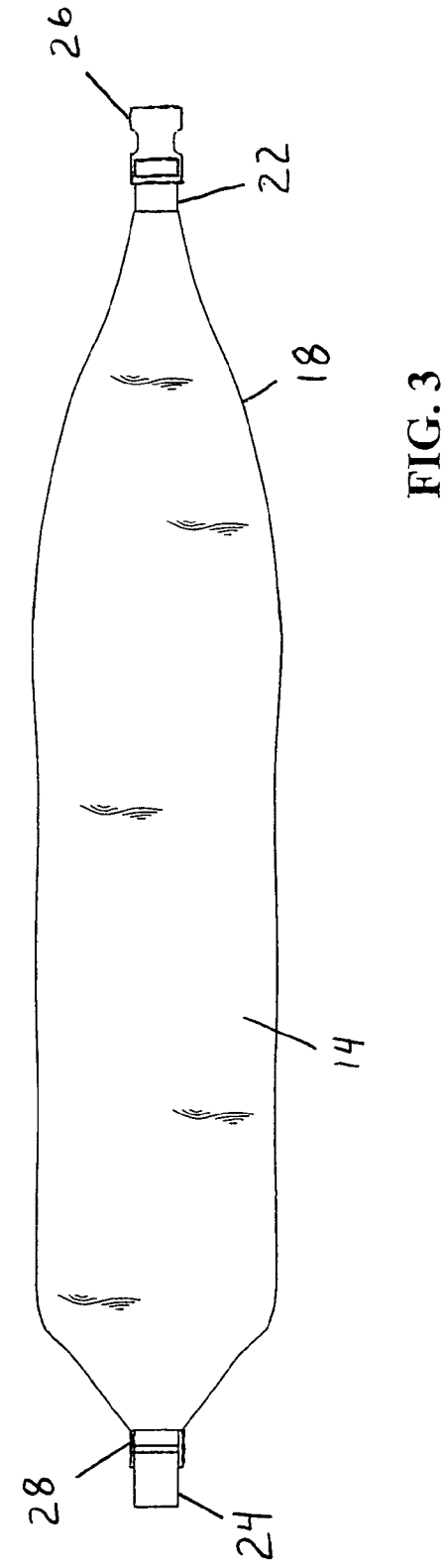

PROTECTIVE SLING

BACKGROUND

1. Field of the Disclosure

The present disclosure relates to a protective sling for supporting and immobilizing a person's injured arm. In particular, the present disclosure relates to a sling having a sleeve into which a person's forearm, particularly a child's forearm surrounded or partially surrounded by a cast or brace, is placed so that the weight of the injured arm is supported about the shoulder and neck of the patient providing greater comfort. Additionally, the sling of the present disclosure is not easily removed from position by the patient, thus maintaining proper immobilization of the injured arm. Further, the hand of the person is covered by the sling, preventing a child from manipulating or destroying the cast or brace.

2. Description of the Related Art

Slings are used to support a person's arm after injury. In many instances, the sling must support a forearm to which a cast or brace has been applied to immobilize the forearm. In such cases, the person's hand is normally exposed. A typical sling consists of a pouch into which an injured arm is placed and a strap that is worn around the shoulder and neck. One such typical sling consists of a envelope-type enclosure made of flexible material for supporting an injured arm between the elbow and the hand, while exposing the hand. An envelope-type sling is constructed of either a single piece of folded material or two facing pieces of material that are closed on the bottom and at the elbow end, and open on the top and at the hand end. A strap is connected at one end of the envelope, which when the sling is worn, is proximate to the wearer's elbow, and at the other end of the envelope proximate to, but not supporting or covering, the wearer's hand. The strap supports the sling around the wearer's shoulder and neck, thus immobilizing the injured arm preventing movement and any associated pain if the person cooperates.

Prior slings available today, when applied to a child who is wearing a forearm cast or brace, allows the child to use his/her fingers to manipulate or even destroy the cast or brace material over which the sling is slid. This is because the cast or brace can be seen by the child, who senses the cast or brace as something causing a degree of discomfort. As a result, the child has a tendency to pick at, manipulate or destroy the cast or brace. The present invention overcomes this problem by keeping the cast or brace, and fingers of the child, out of sight of the child, and thus out of the child's mind.

Typical sling straps are of a woven material such as cotton, polyester, or nylon and tend to be of uniform width over the length of the strap. While the strap does have some flexibility, typically the strap is less flexible than the material comprising the envelope. This limited flexibility of the strap results in "pinch points" about the wearer's neck resulting in discomfort. To alleviate the discomfort, the wearer may attempt to reposition the sling, the injured arm or both. This repositioning and movement of the injured arm could result in further injury to the arm or impede the healing process. Additionally, some patients, typically children or the elderly, tend to fidget at the slightest discomfort. Since the purpose of a sling is to immobilize and support an injured arm, it is desirable to avoid any such movement of the arm.

The envelope-type slings currently available typically have harsh and irritating strapping on the sensitive neck area. This discomfort can lead to noncompliance, especially on the part of an unwilling child or geriatric patient (a similar patient group). Envelope-type slings are difficult to keep in position, and are easily removed. This is undesirable in the target patient group. The sling of the present disclosure is easily put on and removed by a caretaker, but is not as easily removed by the patient.

Correct immobilization is imperative to promote healing and decrease discomfort. In currently available slings, children and geriatric patients are unable to maintain this optimal positioning. Even willing and compliant patients must continually adjust an envelope-type sling. The difficulty and frustration of this constant adjustment increases non-compliance. Furthermore, in envelope slings the hand is always exposed, making it difficult for patients, particularly children, to obey doctor's restrictions on hand use.

SUMMARY

The present invention provides a protective sling that distributes the weight of an injured arm supporting a cast or brace over a larger area of the wearer's neck and shoulder, thus reducing the discomfort with wearing such a device. The protective sling reduces pressure points and helps prevent irritation arising from the coarse texture of the cast material, and helps keep the cast clean. The sling provides for a closed end proximate the hand to aid immobilization by preventing the patient from using the hand to manipulate the cast or brace. The sling keeps the cast or brace near the body, while providing sufficient support for a heavy cast or brace.

Another embodiment of the present invention has a flap that allows access to the immobilized hand for observation of blood flow, color, temperature, and edema without compromising this necessary restriction of hand use. Yet another embodiment has an open hand access port allowing for unrestricted hand use, if permitted by the doctor's orders.

BRIEF DESCRIPTION OF THE DRAWINGS

FIG. 2 is a front plan view of the sling of FIG. 1;

FIG. 3 is a rear plan view of the sling of FIG. 1;

DETAILED DESCRIPTION

Figure 1:
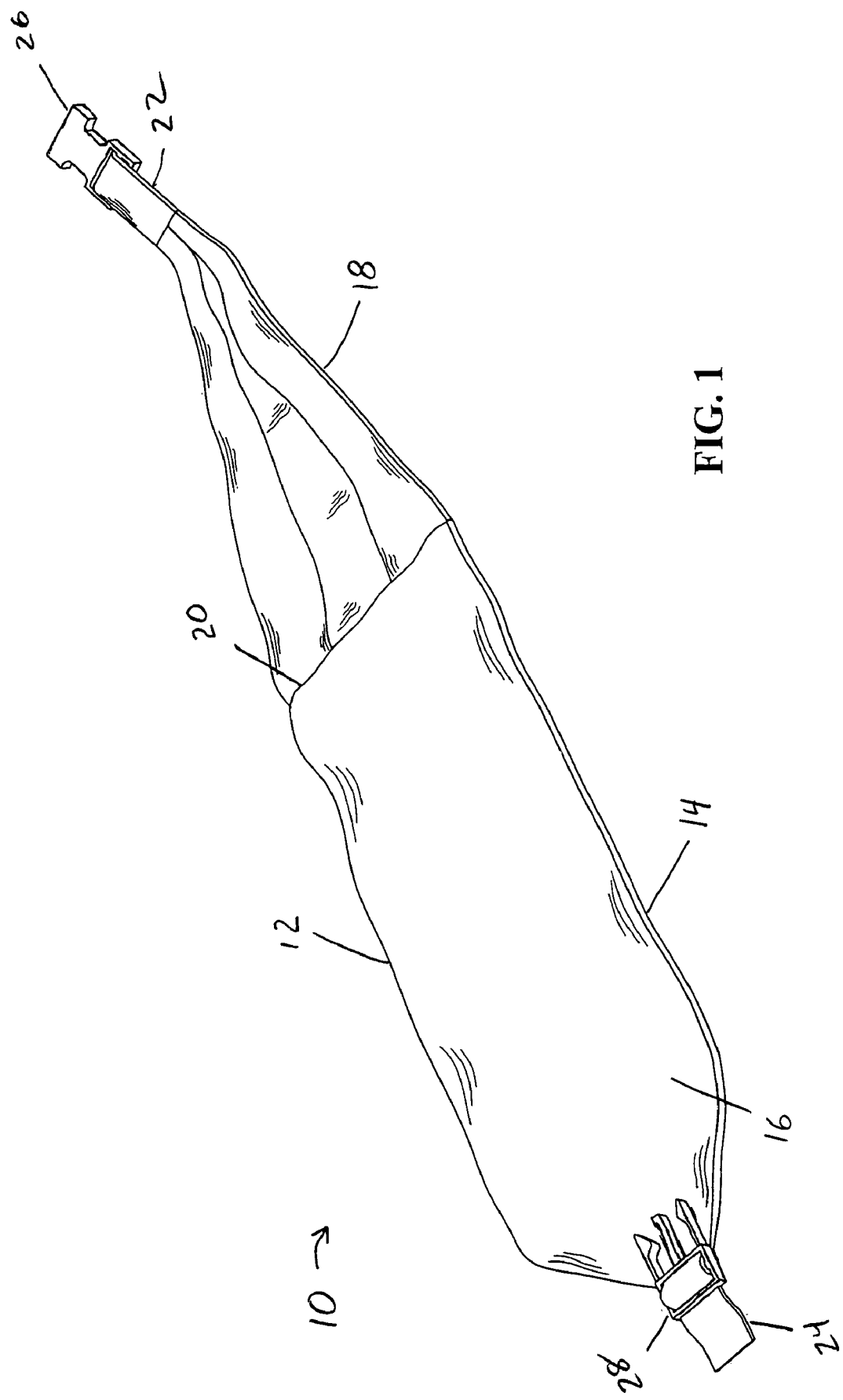
FIG. 1 is a perspective view of an embodiment of the sling of the present invention.

While the present invention may be susceptible to embodiment in different forms, there is shown in the drawings, and herein will be described in detail, embodiments with the understanding that the present description is to be considered an exemplification of the principles of the invention and is not intended to be exhaustive or to limit the invention to the details of construction and the arrangements of components set forth in the following description or illustrated in the drawings.

FIGS. 1–3 illustrate a first embodiment of a protective sling 10 of the present invention. Sling 10 is made of a soft, flexible fabric material such as cotton, polyester, nylon and the like. Sling 10 has a protective sleeve portion 12 and a harness portion 18. The sleeve portion of this particular embodiment is formed from two panels of flexible fabric material. The first panel 14 is of predetermined length, sized generally to support the cast or brace bearing forearm of a person from the elbow to the hand. The second panel 16 partially overlies and is of shorter length than the first panel 14. In an embodiment of the present disclosure, the portion of first panel 14 that extends beyond second panel 16 may be tapered along its length as shown in FIGS. 1–3. Alternatively, first panel 14 may be of constant width along its length.

The first panel 14 and the second panel 16 are joined together at their periphery by suitable means known in the art such as stitching to form a sleeve 12 with an opening 20 being positioned proximate to the extended portion of first panel 14. The end of sleeve 12 opposite the opening is completely closed. Attached to the end of the extended portion and to the closed end of the sleeve are strap assemblies. In the embodiment shown, the strap assemblies are formed from strips of webbing material 22, 24, and fasteners 26, 28 which releasably join the closed or hand-end of the sleeve 12 with the extended end 18 of the first panel 14. In the embodiment shown, the fasteners 26, 28 are mating portions of typical clasp buckles that allow for adjusting the length of webbing 22 and 24.

In use, the cast or brace bearing forearm of the patient is slid into the sleeve 12. The entire cast or brace, or substantially all of the cast or brace, is covered by sleeve 12, with the hand of the patient lodged out of sight in the closed end of sleeve 12. Harness 18 is extended around the shoulder and neck of the patient, and fasteners 26 and 28 are joined. The sling 10 will support the cast or brace covered arm close to the patient's body, while preventing the arm from substantial movement. The hand of the patient is lodged inside the closed end of sleeve 12, and is not available to be used to pick on or destroy the cast or brace.

Figure 4:
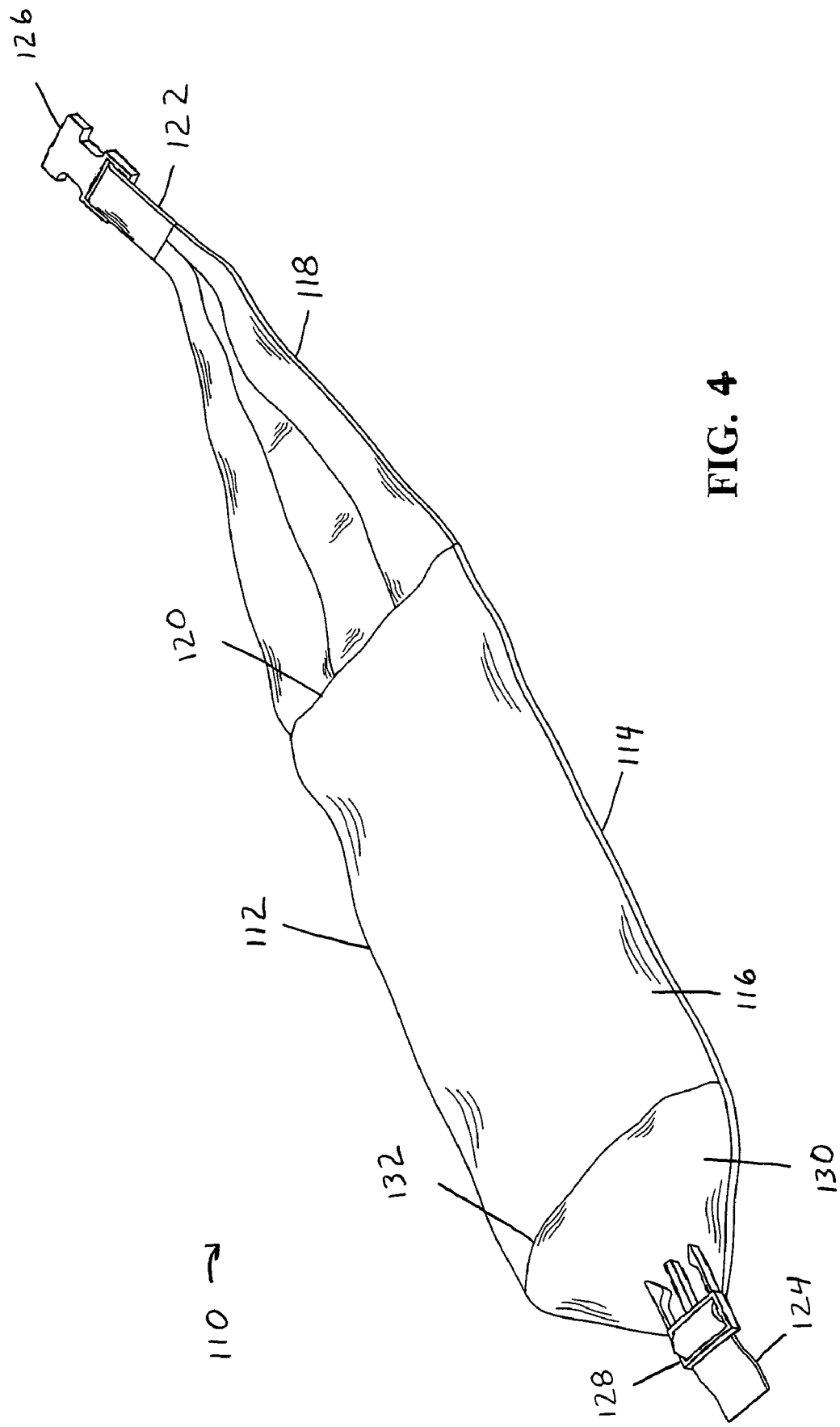
FIG. 4 is perspective view of another embodiment of the sling of the present disclosure having a flap to access a wearer's hand and fingers.
Figure 5:
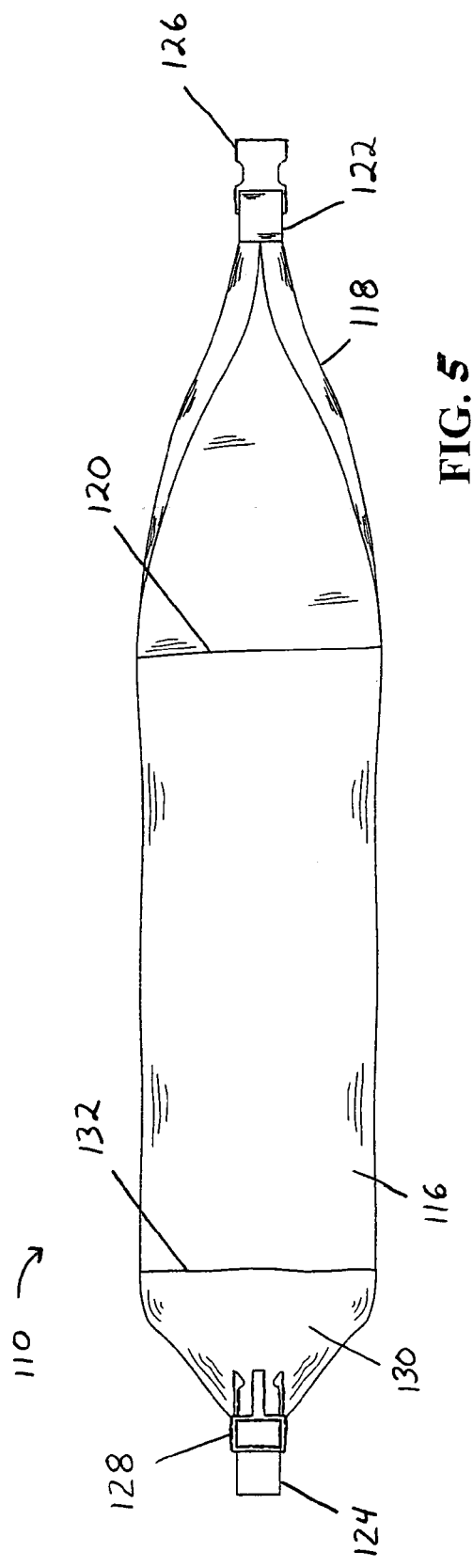
FIG. 5 is a front plan view of the sling of FIG. 4.
Figure 6:
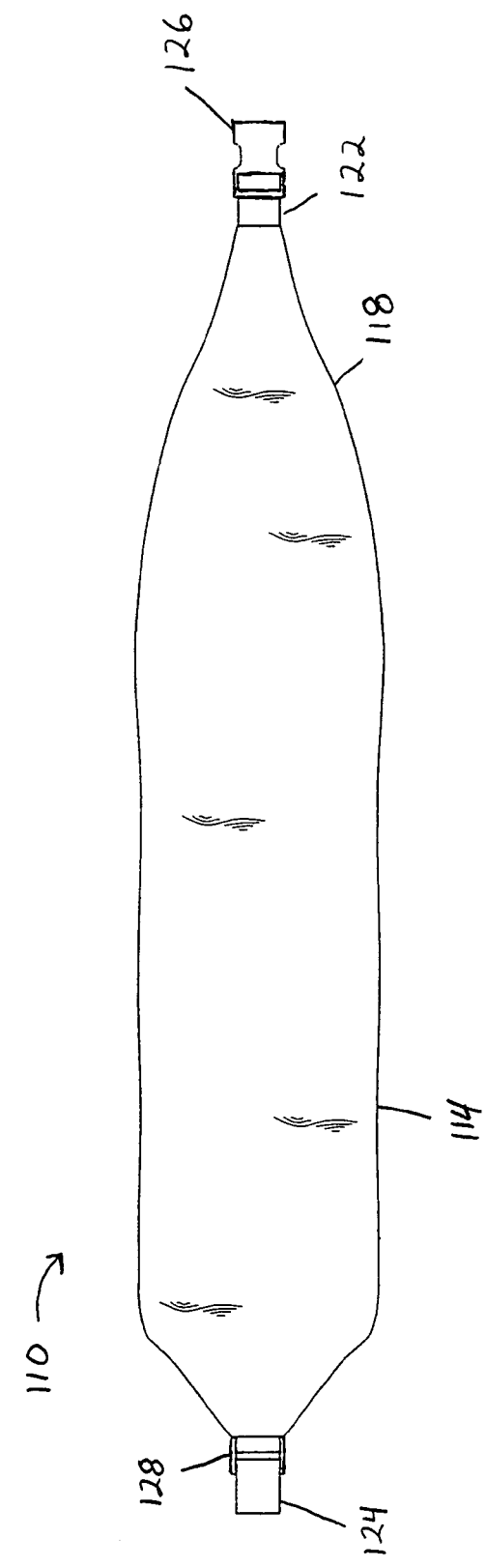
FIG. 6 is a rear plan view of the sling of FIG. 4.

Another embodiment of the present disclosure shown in FIGS. 4–6 is similar to the first embodiment but with a flap 132 forming a closable second opening in sleeve 112 opposite opening 120 for access to the hand and fingers without moving the arm. Sling 110 is made of a soft flexible fabric material such as cotton, polyester, nylon and the like. Sling 110 has a protective sleeve portion 112 and a harness portion 118. The sleeve portion 112 of this particular embodiment is formed from three panels of soft flexible fabric material. The first panel 114 is of predetermined length. The second panel 116 partially overlies and is shorter than the first panel 114. Second panel 116 is generally sized to support the forearm of a person from the elbow to the hand. First panel 114 has a body portion which is generally matches the size and shape of second panel 116, and an extended portion 118 which extends from the sleeve 112.

The first panel 114 and the second panel 116 are joined together at their periphery by suitable means known in the art such as stitching forming sleeve 112 with an opening 120 being positioned proximate to the extended portion of first panel 114. A third panel 130 partially overlies and is joined to the first panel 114 and the second panel 116. Third panel 130 overlapping second panel 116 forms a flap 132 which may be folded out of the way allowing an opening to provide access to the hand for evaluation of blood flow, color, temperature, edema and other characteristics without compromising the necessary immobilization of the hand.

Attached to the end of the extended portion 118 and to the closed end of the sleeve are strap assemblies. In this embodiment, the strap assemblies are formed from strips of webbing material 122, 124, and fasteners 126, 128 which releasably join the hand-end of the sleeve 112 with the extended end of harness 118. In the embodiment shown, the fasteners 126, 128 are mating portions of typical clasp buckles that allow for adjusting the length of webbing 122 and 124.

In use of the embodiment of FIGS. 4-6, the cast or brace bearing forearm of the patient is slid into the sleeve 112. The entire cast or brace, or substantially all of the cast or brace, is covered by sleeve 112, with the hand of the patient lodged out of sight in the closed end of sleeve 112 beneath flap 132. Harness 118 is extended around the shoulder and neck of the patient, and fasteners 126 and 128 are joined. The sling 110 will support the cast or brace covered arm close to the patient's body, while preventing the arm from substantial movement. The hand of the patient is lodged inside the closed end of sleeve 112 adjacent flap 132, and is not available to be used to pick on or destroy the cast or brace. If necessary, the flap 132 may be opened to provide examination of the hand for proper blood flow, color, temperature, edema or the like. Also, if required, the patient's hand may extend out of the flap 132 for the purpose of gripping an implement, such as a writing utensil or the like.

In yet another embodiment (not shown) the sleeve portion is open at the hand end. This configuration allows for support of the patient's forearm and use of the hand when permitted by doctor's orders.

In this embodiment of a protective sling, the sling is again made of a soft, flexible fabric material such as cotton, polyester, nylon and the like. The sling has a protective sleeve portion and a harness portion. The sleeve portion of this particular embodiment is formed from two panels of flexible fabric material. The first panel is of predetermined length. The second panel partially overlies and is of shorter length than the first panel. The second panel is sized generally to support the forearm of a person from the elbow to the hand. The first panel and the second panel are joined together at their periphery by suitable means already described with a first opening being positioned proximate to the extended portion of the first panel. The end of the sleeve opposite the first opening has a second opening, allowing the patient to use the hand when immobilization is not required. Attached to the end of the extended portion and to the closed end of the sleeve are strap assemblies as previously described.

While embodiments have been illustrated and described in the drawings and foregoing description, such illustrations and descriptions are considered to be exemplary and not restrictive in character, it being understood that only illustrative embodiments have been shown and described and that all changes and modifications that come within the spirit of the invention are desired to be protected. The applicant has provided description and figures which are intended as an illustration of certain embodiments of the disclosure, and are not intended to be construed as containing or implying limitation of the disclosure to those embodiments. There are a plurality of advantages of the present disclosure arising from various features set forth in the description. It will be noted that alternative embodiments of the disclosure may not include all of the features described yet still benefit from at least some of the advantages of such features. Those of ordinary skill in the art may readily devise their own implementations of the disclosure and associated methods that incorporate one or more of the features of the disclosure and fall within the spirit and scope of the present disclosure.

I claim:

1. A protective sling adapted to support a cast or brace extending adjacent a forearm and wrist of a patient, and to selectively simultaneously support a hand of a patient, the sling comprising:

a flexible material having a first portion extending a predetermined length, and a second portion partially overlying a length of the first portion and forming a first opening into a unitary tubular sleeve, the sleeve disposed between the first portion and the second portion and defining a longitudinal sleeve axis therebetween, wherein the first opening is oriented substantially perpendicular to the sleeve axis;

the sleeve having a closed end opposite to and spaced from the first opening between the first and second portions forming the sleeve;

a strap assembly attached to the closed end and to an opposite end of the protective sling, the strap assembly comprising a first flexible material strip with a first fastener disposed at the closed end and a second flexible material strip with a second fastener disposed at the opposite end, wherein the first fastener is adapted to releasably engage the second fastener, the strap assembly adapted to extend adjacent the neck and a shoulder of the patient, suspending the protective sling adjacent the body of the patient;

a second opening into the sleeve formed in the second portion of the flexible material; the second opening located between the first opening and the closed end of the sleeve, wherein said first opening and said second opening are substantially parallel; and the sleeve being adapted to receive and support the hand of the patient adjacent the closed end of the sleeve, and the second opening providing access to the hand and into the exterior of the protective sling.

2. The protective sling of claim 1 wherein the second opening is disposed closer to the closed end than to the first opening.

3. The protective sling of claim 2 further comprising:

a third portion of flexible material extending from adjacent the termination of the second portion to the end of the first portion, the third portion overlapping a portion of the first portion forming a flap for closing the second opening.

4. A protective sling adapted to support a cast of brace extending adjacent a forearm and wrist of a patient while allowing access to the patient's hand, the sling comprising:

a flexible material having a first portion extending a predetermined length, and a second portion partially overlying the length of the first portion and forming a first opening into a unitary tubular sleeve, the sleeve disposed between the first portion and the second portion and defining a longitudinal sleeve axis therebetween, wherein the first opening is oriented substantially perpendicular to the sleeve axis;

the sleeve having a second opening opposite to and spaced from the first opening, between the first and second portions, wherein the first and second openings are substantially parallel; and a strap assembly attached adjacent to the second opening and to an opposite end of the protective sling, the strap comprising a first flexible material strip with a first fastener disposed at the closed end and a second flexible material strip with a second fastener disposed at the opposite end, wherein the first fastener is adapted to releasably engage the second fastener, the strap assembly adapted to extend adjacent the neck and shoulder of the patient, suspending the protective sling adjacent the body of the patient and wherein the sleeve is adapted to receive, enclose and support the forearm of the patient while allowing access to the hand through the second opening.

* * * * *